(12) United States Patent
Kumar et al.

(10) Patent No.: US 9,113,816 B2
(45) Date of Patent: Aug. 25, 2015

(54) SYSTEM AND METHOD FOR PROSTATE BIOPSY

(71) Applicant: Eigen, Inc., Grass Valley, CA (US)

(72) Inventors: Dinesh Kumar, Grass Valley, CA (US); Jasjit S. Suri, Roseville, CA (US)

(73) Assignee: EIGEN, INC., Grass Valley, CA (US)

( * ) Notice: Subject to any disclaimer, the term of this patent is extended or adjusted under 35 U.S.C. 154(b) by 240 days.

(21) Appl. No.: 13/665,595

(22) Filed: Oct. 31, 2012

(65) Prior Publication Data

US 2013/0116548 A1 May 9, 2013

Related U.S. Application Data

(63) Continuation-in-part of application No. 12/615,862, filed on Nov. 10, 2009, now abandoned.

(60) Provisional application No. 61/113,479, filed on Nov. 11, 2008.

(51) Int. Cl.

| *A61B 8/00* | (2006.01) |
|---|---|
| *A61B 8/08* | (2006.01) |
| *A61B 10/02* | (2006.01) |
| *A61B 5/00* | (2006.01) |
| *A61B 8/12* | (2006.01) |
| *A61B 19/00* | (2006.01) |
| *G06T 7/00* | (2006.01) |

(52) U.S. Cl.
CPC .............. *A61B 8/0841* (2013.01); *A61B 5/4381* (2013.01); *A61B 8/12* (2013.01); *A61B 8/463* (2013.01); *A61B 8/466* (2013.01); *A61B 8/483* (2013.01); *A61B 8/523* (2013.01); *A61B 8/5207* (2013.01); *A61B 8/5253* (2013.01); *A61B 10/02* (2013.01); *A61B 10/0241* (2013.01); *A61B 19/5244* (2013.01); *G06T 7/0028* (2013.01); *A61B 2019/5278* (2013.01); *G06T 2207/10072* (2013.01); *G06T 2207/10132* (2013.01); *G06T 2207/30021* (2013.01); *G06T 2207/30056* (2013.01); *G06T 2207/30068* (2013.01); *G06T 2207/30081* (2013.01); *G06T 2207/30084* (2013.01)

(58) Field of Classification Search
CPC ............... A61B 10/02; A61B 10/0241; A61B 19/5244; A61B 2019/5278; A61B 5/4381; A61B 8/0841; A61B 8/12; A61B 8/463; A61B 8/466; A61B 8/483; A61B 8/5207; A61B 8/523; A61B 8/5253; G06T 2207/10072
USPC .......................................... 600/443; 382/128
See application file for complete search history.

(56) References Cited

U.S. PATENT DOCUMENTS 5,931,787 A * 8/1999 Dietz et al. .................... 600/461
6,022,325 A * 2/2000 Siczek et al. .................. 600/568

(Continued)

*Primary Examiner* — Jonathan Cwern
(74) *Attorney, Agent, or Firm* — Marsh Fischmann & Breyfogle LLP

(57) ABSTRACT

The invention presents tools to improve a 3-D image aided biopsy or treatment procedure for prostate gland by providing additional functionality and additional visual cues on an output image of the prostate, which may be generated substantially in real-time. The tools include i) the identification of various parts of prostate to classify as per regular classification in pathological reports, ii) Computing and displaying the insertion depth of needle with respect to a selected target point during the procedure, iii) Computing and displaying the distance from needle tip to prostate surface following a procedure and, iv) Calibration for misalignment of a 2-D imaging transducer when used under tracked motion for a procedure.

11 Claims, 12 Drawing Sheets

(56) References Cited

U.S. PATENT DOCUMENTS

2007/0219448 A1* 9/2007 Seip et al. .................... 600/454
2009/0048515 A1* 2/2009 Suri et al. .................... 600/443
2009/0093715 A1* 4/2009 Downey et al. ............... 600/437

* cited by examiner

SYSTEM AND METHOD FOR PROSTATE BIOPSY

CROSS-REFERENCE TO RELATED APPLICATION

This application is a continuation-in-part of U.S. patent application Ser. No. 12/615,862 having a filing date of Nov. 10, 2009 and which claims priority under 35 U.S.C. 119 to U.S. Provisional Application No. 61/113,479, entitled: "Improved System and Method for Prostate Biopsy," filed on Nov. 11, 2008, the contents of both of which are incorporated herein as if set forth in full.

BACKGROUND

When cancer is suspected on an organ such as a breast, prostate, kidney or liver, a common diagnostic tool is to take biopsies of the organ tissue. A cancer may only be present in a very small portion of the organ in the early stages of its growth. However, this generally represents the stage when it is most desirable to detect the cancer. Cancer may also be uncorrelated and therefore may be present in a very small portion of the organ but at multiple places. Therefore the decision of where in the organ to take a biopsy will have a significant impact on successful early detection of a cancer as well as increasing the confidence of a negative result.

Maximum confidence in a biopsy outcome is currently only possible if the organ has been sampled at a multitude of locations. This technique is known as saturation biopsy and the number of core sites can reach 90 or more. Such saturation biopsy often causes considerable discomfort to the patient. Further, smaller organs such a prostate, which may only be 4 cm in diameter, may be damaged by sampling at numerous biopsy sites required for a saturation biopsy. However, as the number of biopsy sites decreases, so does the probability of an accurate result.

Management of biopsy targets is critical to a successful procedure. The operator must be able to plan each biopsy core site location, be able to accurately navigate the needle to each site to take the biopsy and finally to record the actual location of the biopsy site for future reference. This becomes overwhelming when a large number of sites are used. When a patient returns for multiple repeat visits the amount of data and complexity is increased proportionally.

SUMMARY OF THE INVENTION

The presented inventions pertain to improving workflow and proving additional information to a physician for an image guided procedure on prostate gland. The tools and methods described mostly pertain to application to cancer diagnosis (image guided biopsy) and treatment (image guided dose delivery). Prostate cancer is one of the most common causes of cancer among men and the diagnosis includes PSA level test, DRE test and biopsy. So far, prostate biopsy has been found to be only conclusive way to confirm presence of cancer in the gland. Typically, a biopsy is performed under guidance of a 2-D ultrasound image either trans-rectally or trans-perineally. A transrectal ultrasound transducer is often used for such a procedure. Some ultrasound machines allow viewing of more than one plane at a time to assist needle insertion during biopsy. Recently, 3-D image guidance has been applied to prostate biopsy such that the prostate can be sampled in a desired fashion. Such approaches require acquisition of 3-D image, which may be reconstructed from a sequence of uniformly spaced 2-D frames acquired from the ultrasound transducer. The uniform spacing may be either linear or rotational. These approaches require a tracking device to measure the location and orientation of ultrasound transducer during the procedure so that the correspondence between the live video from ultrasound machine with respect to the acquired 3-D image is known.

Similar developments have been made in field of prostate treatment using image guidance, where a 3-D image of prostate gland may be acquired prior to a procedure. The treatment plan is then made from the 3-D image, which may be acquired using an imaging technique other than ultrasound. For example, a treatment plan may be based on MRI or CT image acquired earlier. The invention applies to a number of treatment procedures and tools described provide workflow enhancements in a general sense. The prostate boundaries may further be extracted from the 3-D image for performing dose computations. In many procedures where the plan was based on 3-D image, the imaging modality during the procedure is still 2-D ultrasound. The correspondence of field of view (2-D ultrasound frame) with the 3-D image is either fixed by design or computed using a tracking device such that there is a clear method for reaching the desired target locations as per the 3-D image-based plan. Aspects of the presented invention aim to make the following workflow enhancements:

1. Dividing prostate into regions
2. Distance measurements during a procedure
   a. Distance of planned point from prostate boundaries
   b. Automatic plan based on uniform sampling of prostate
   c. Distance measurement from prostate boundaries on live 2-D ultrasound image before needle insertion
   d. Distance measurements from prostate boundaries after a needle insertion
3. Alignment correction for hardware misalignments.

The inventions provide systems and methods for 3D image guided biopsy, where the urethra can be delineated in a 3-D image of prostate. The urethra may be manually delineated using a series of control points along it using multiple views of the prostate gland. Alternatively, it may be fully automatically or semi-automatically segmented.

In another arrangement, the systems and methods of the inventions, in various aspects, may also contain a subsystem for automatic or semi-automatic segmentation of prostate. Using this information, the base and apex of the prostate can be identified as intersection of the urethra with the prostate surface. After identification of base and apex, the system can divide the prostate into a number of zones—Left/Right/Left Lateral/Right Lateral, Base/Mid/Apex.

The systems and methods of the inventions may, in various aspects, provide a method for identification of various zones that can be displayed overlaid on the prostate 3-D image using a color scheme such that one color corresponds to one zone. Each zone may be selectable and turned on one at a time.

The systems and methods of the inventions may, in various aspects, provide a method for identification of the zones and usage of zonal information to plan a biopsy or treatment procedure for prostate gland by selecting a zone and placing point in it.

The systems and methods of the inventions may, in various aspects, may provide a system for computing prostate zones for 3-D transrectal ultrasound guided biopsy such that the zonal information may be used to automatically place a point at centroid of each such zone, thus creating a template for targeted biopsy based on the partitioning of a patient's prostate and customized to the shape of that particular prostate.

The systems and methods of the inventions may, in various aspects, also provide methods for identification and reporting the zone for a sampled core following a procedure and recording of actual location of a sampled or treated site. The definition of zones can be adjusted based on how a physician might collect samples from the prostate.

The systems and methods of the inventions may, in various aspects, may also provide visual aids to the user for needle insertion for a biopsy or treatment procedure such as brachytherapy by displaying needle insertion depth. The visual aids are provided to the user for needle insertion for a procedure on prostate for reaching a pre-planned target point corresponding to either a biopsy sampling point or a point for dose delivery under a treatment procedure (such as brachytherapy, cryotherapy, thermal ablation). The target point may be planned on a 3-D image acquired earlier and the needle may be guided to the target point under navigation through a tracking device. The visual aids include displaying the target point planned in 3-D overlaid on the live view by applying the transforming from 3-D frame of reference to the 2-D live video. The overlay is displayed only when the target point is computed to be within a small distance (e.g.; 5 mm) from the 2-D frame corresponding to the live video.

The systems and methods of the inventions may, in various aspects, provide visual aids to the user for needle insertion for a procedure on prostate for reaching a pre-planned target point corresponding to either a biopsy sampling point or a point for dose delivery under a treatment procedure (such as brachytherapy, Cryotherapy, thermal ablation). The target point may be planned on a 3-D image acquired earlier and the needle may be guided to the target point under navigation through a tracking device. For a given target point and needle type, the system displays how deep the needle should be inserted before firing such that after firing, the planned site lies at the center of the needle core (or bead location for brachytherapy). It may be desirable to know this information before firing, since there are cases when a physician may not want to overshoot the needle and damage neighboring organ by placing a radioactive seed there or piercing it.

The systems and methods of the inventions may, in various aspects, provide visual aids to the user for needle insertion for a procedure on prostate for reaching a pre-planned target point corresponding to either a biopsy sampling point or a point for dose delivery under a treatment procedure (such as brachytherapy, cryotherapy, thermal ablation). It may not always be possible for a user to plan placement of radioactive seeds or plan biopsy targets in advance such that needle avoids certain anatomical structures such as organs (bladder, urethra) or nerve bundles. Additional visual cues are provided in this system to facilitate a procedure based on just prostate shape. The system displays a ruler representing the distance from the prostate surface at the further end from the needle entry point along the needle trajectory. The system may, at any time, display a ruler from the distal surface (anterior for a transrectal procedure, for example) such that the user always knows how deep the user is inserting the needle relative to the prostate boundaries along the needle trajectory.

The methods are provided for computing and displaying the distance of the needle tip with respect to the prostate surface following a procedure and recording of actual location of a sampled or treated site. Likewise, the system can compute the distance of the actual core taken from the prostate surface.

The systems and methods of the inventions may, in various aspects, also include a subsystem for computing distance from prostate boundaries to facilitate planning. In this subsystem, the system computes and displays the distance of a planned location for sampling a site or placement of radioactive seeds or applicator. Additionally, the system and methods may compute and display iso-surfaces at user-selected distances from prostate surface so as to assist the user in planning and during the procedure. There may be a number of iso-surfaces at user-selected distances from prostate surface to assist the user in planning and during the procedure. For some biopsy procedures, user may want to sample only points within a certain distance from the boundaries of the prostate and a colored iso-surface inside the surface representing the prostate boundaries allows them to do this. In addition, the systems and methods may compute and display the iso-surfaces overlaid on the grayscale image such that a combination of intensity information and boundary information can be utilized in planning a procedure. The computation of distances in 3-D makes it easier for user to interpret 2-D image slices typically seen during planning.

The systems and methods of the inventions may, in various aspects, also have a subsystem to compute a plan automatically using a user-selected uniform spacing for a procedure, based on prostate boundaries. This makes it easier for procedures where user has to plan uniformly over the prostate for either a biopsy or treatment procedure.

The systems and methods of the inventions, in various aspects, may also have a subsystem to compute a plan automatically using a user-selected uniform spacing for a procedure, based on prostate boundaries. This makes it easier for procedures where user has to plan uniformly over the prostate for either a biopsy or treatment procedure. In addition, the automatic loading of such a plan also takes into consideration the regions where placing of points is undesirable by avoiding locations close to structures such as urethra and nerve bundles, if such an information is available.

BRIEF DESCRIPTION OF DRAWINGS

FIG. 7 represents various measurements needed to identify the zone a planned site is placed in.

DETAILED DESCRIPTION

Reference will now be made to the accompanying drawings, which assist in illustrating the various pertinent features of the various novel aspects of the present disclosure. Although the invention is described primarily with respect to an ultrasound imaging embodiment, the invention is applicable to a broad range of imaging modalities and biopsy techniques, including MRI, CT, and PET, which are applicable to organs and/or internal body parts of humans and animals. In this regard, the following description is presented for purposes of illustration and description. Furthermore, the description is not intended to limit the invention to the form disclosed herein. Consequently, variations and modifications commensurate with the following teachings, and skill and knowledge of the relevant art, are within the scope of the present invention.

Figure 1:
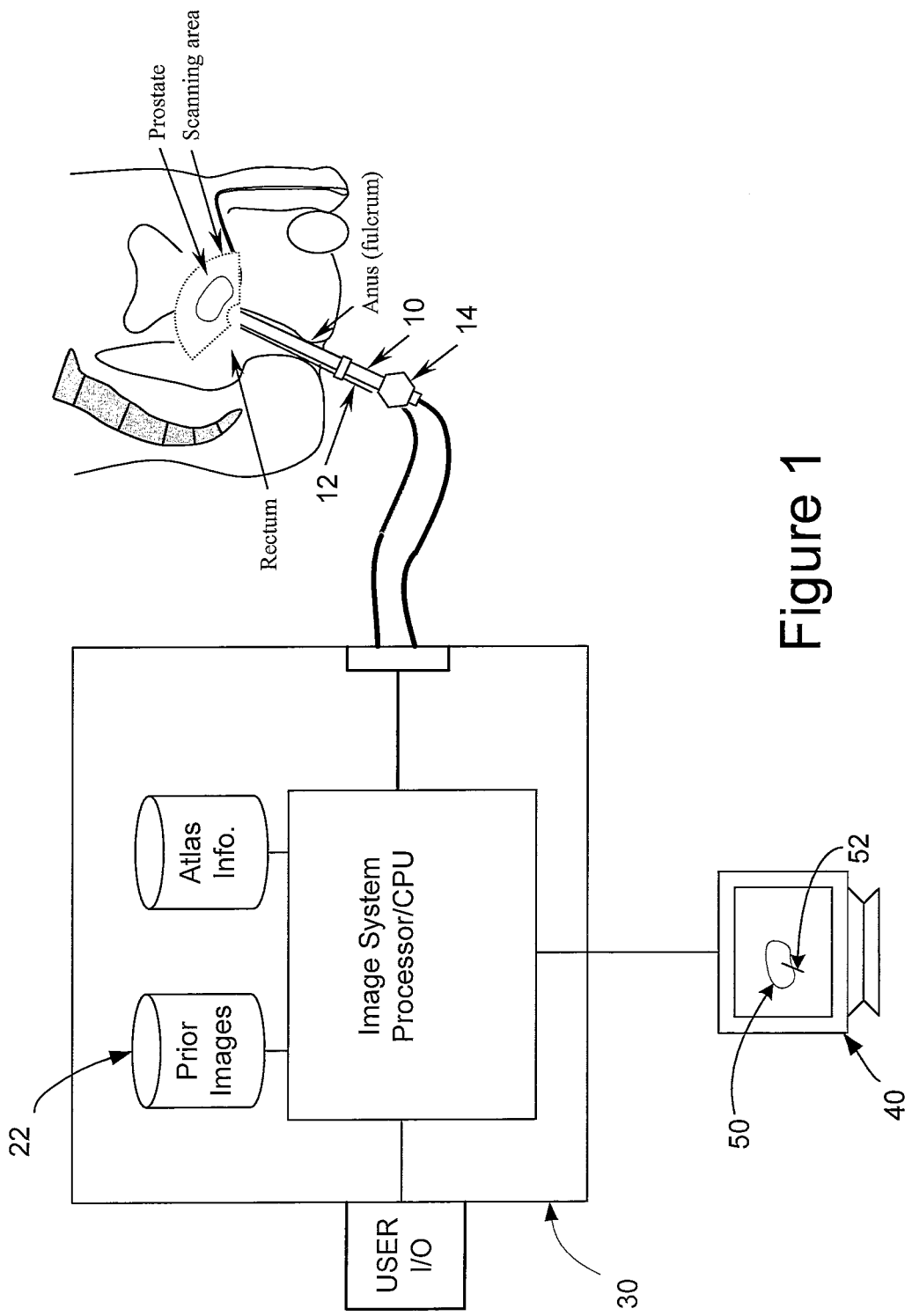
FIG. 1 illustrates a prostate imaging system.

Initially, an exemplary embodiment of the invention will be described in relation to performing prostate biopsy using transrectal ultrasound (TRUS) guidance. As shown in FIG. 1. The ultrasound probe 10 has a biopsy needle assembly 12 attached to its shaft inserted into the rectum from the patient's anus. The probe 10 is an end-fire transducer that has a scanning area of a fan shape emanating from the front end of the probe (shown as a dotted outline). The probe handle is held by a robotic arm or motion constraining tracker assembly (not shown) that has a set of position sensors 14. One exemplary tracker assembly is set forth in International Application No. PCT/CA2007/001076, entitled "Apparatus for guiding a medical tool" the contents of which is incorporated by reference herein. These position sensors 14 are connected to the computer 20 of the imaging system 30 via an analog to digital converter. Hence, the computer 20 has real-time information of the location and orientation of the probe 10 in reference to a unified Cartesian (x, y, z) coordinate system.

Figure 2:
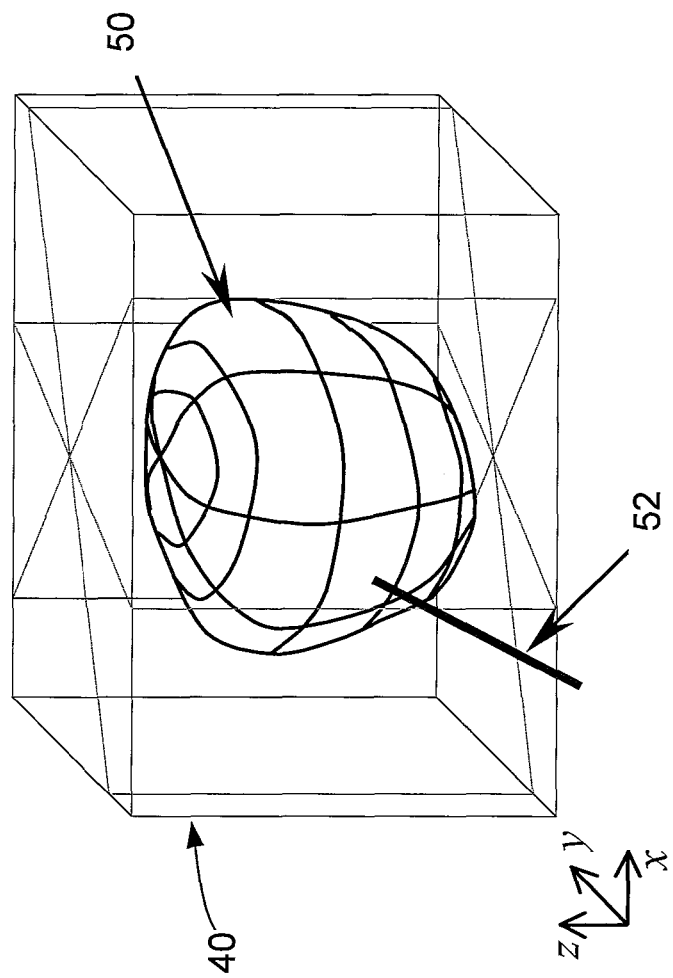
FIG. 2 illustrates an output with a display device of the prostate imaging system.

With the dimensions of the probe 10 and needle assembly 12 taken into the calculations, the 3D position of the needle tip and its orientation is known. The ultrasound probe 10 sends signal to the ultrasound system 30, which may be connected to the same computer (e.g., via a video image grabber) as the output of the position sensors 14. In the present embodiment, this computer is integrated into the imaging system 30. The computer 20 therefore has real-time 2D and/or 3D images of the scanning area in memory 22. The image coordinate system and the robotic arm coordinate system are unified by a transformation. Using the acquired 2D images, a prostate surface 50 (e.g., 3D model of the organ) and biopsy needle 52 are simulated and displayed on a display screen 40 with their coordinates displayed in real-time as best shown in FIG. 2. A biopsy needle may also be modeled on the display, which has a coordinate system so the doctor has the knowledge of the exact locations of the needle and the prostate.

The computer system runs application software and computer programs which can be used to control the system components, provide user interface, and provide the features of the imaging system. The software may be originally provided on computer-readable media, such as compact disks (CDs), magnetic tape, or other mass storage medium. Alternatively, the software may be downloaded from electronic links such as a host or vendor website. The software is installed onto the computer system hard drive and/or electronic memory, and is accessed and controlled by the computer's operating system. Software updates are also electronically available on mass storage media or downloadable from the host or vendor website. The software, as provided on the computer-readable media or downloaded from electronic links, represents a computer program product usable with a programmable computer processor having computer-readable program code embodied therein. The software contains one or more programming modules, subroutines, computer links, and compilations of executable code, which perform the functions of the imaging system. The user interacts with the software via keyboard, mouse, voice recognition, and other user-interface devices (e.g., user I/O devices) connected to the computer system.

Once the biopsy sites are selected, biopsy sample collection is preformed such that extracted tissues may be provided for pathological tests. As the position of the biopsy needle may be know in relation to the ultrasound image, the locations within the prostate from which biopsy samples are extracted may be saved into the ultrasound image. Once all biopsy locations are saved into the image, the composite image including the information associated with the biopsy locations may be stored for future use.

Biopsies are typically performed with a thin, 18-guage needle mounted on a spring-loaded gun connected to the ultrasound probe, forcing the needle to stay in the imaging plane so that it is always visible in the ultrasound image. Such needles typically take biopsy cores that are approximately 19 mm long and 1.8 mm in diameter. However, different sized cores may be taken with different sized needles and are within the scope of the present invention. Each core is separately identified as to its location, so that the pathologist can report the extent and grade of cancer or other cells of interest. Further, each core sample is marked to identify the end closest to the needle gun, or the end farthest from the needle gun. It is, therefore, desirable to know exactly where the initial sample was obtained in order to target more relevant tissue if a repeat biopsy is performed.

Dividing Prostate into Regions

Figure 3:
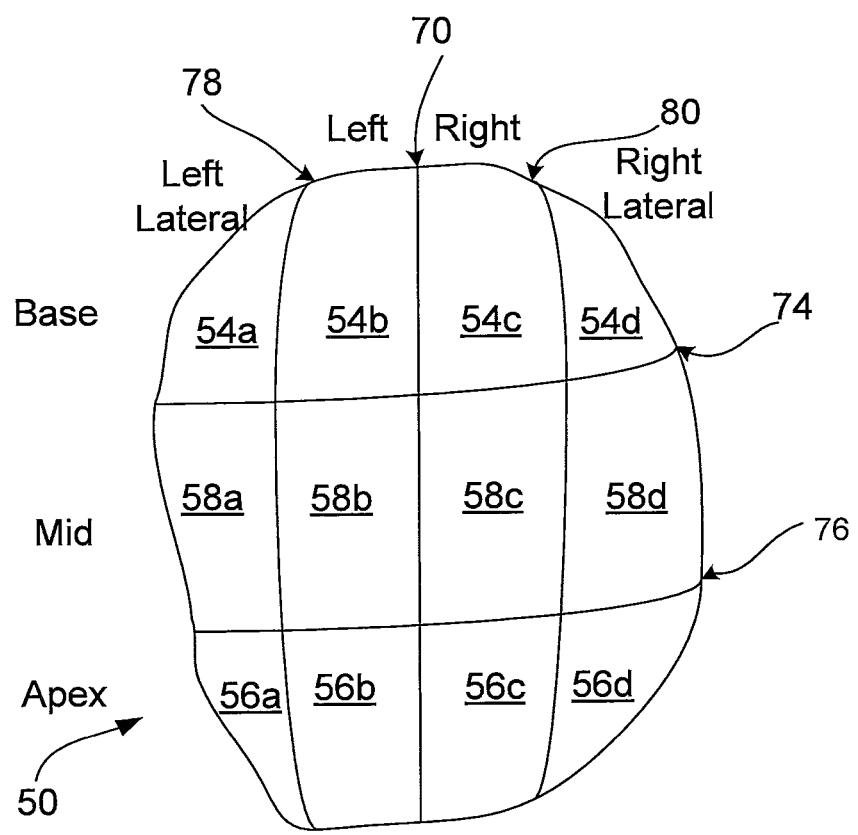
FIG. 3 represents a typical zonal division of prostate used by many urologist as a map for 12-core biopsy.

A large number of custom biopsy plans used by physicians depend upon their interpretation of different prostate regions and many pathology reports report findings as such. FIG. 3 illustrates an example of regions in a prostate image 50, which may be used to perform a biopsy. The figure shows a transverse view such that the top of image represents base 54 of the prostate and the bottom represents the apex 56 of the prostate. The image shows 12 zones: left-lateral-base 54A, left-lateral-mid 58A, left-lateral-apex 56A, left-base 56B, left-mid 58B, left-apex 56B, right-base 54C, right-mid 58C, right-apex 56C, right-lateral-base 54D, right-lateral-mid 58D and right-lateral-apex 56D. The image is representative of a biopsy plan. Different types of plans may be included provided that they are in some relation to the shape and orientation of the prostate. The zone identification subsystem in presented inventions not only computes the zones based on a urethra delineation or segmentation, but also can compute and report the zones for sampled biopsy cores. The definition of zones may be adjustable as per user's preferences, for example if the user wishes to only distinguish between left and right, the system can be adjusted by the user accordingly. As a result, the zone identification subsystem is very useful to do a planning as well as after the procedure such that the true region is reported in the pathology report.

Figure 4:
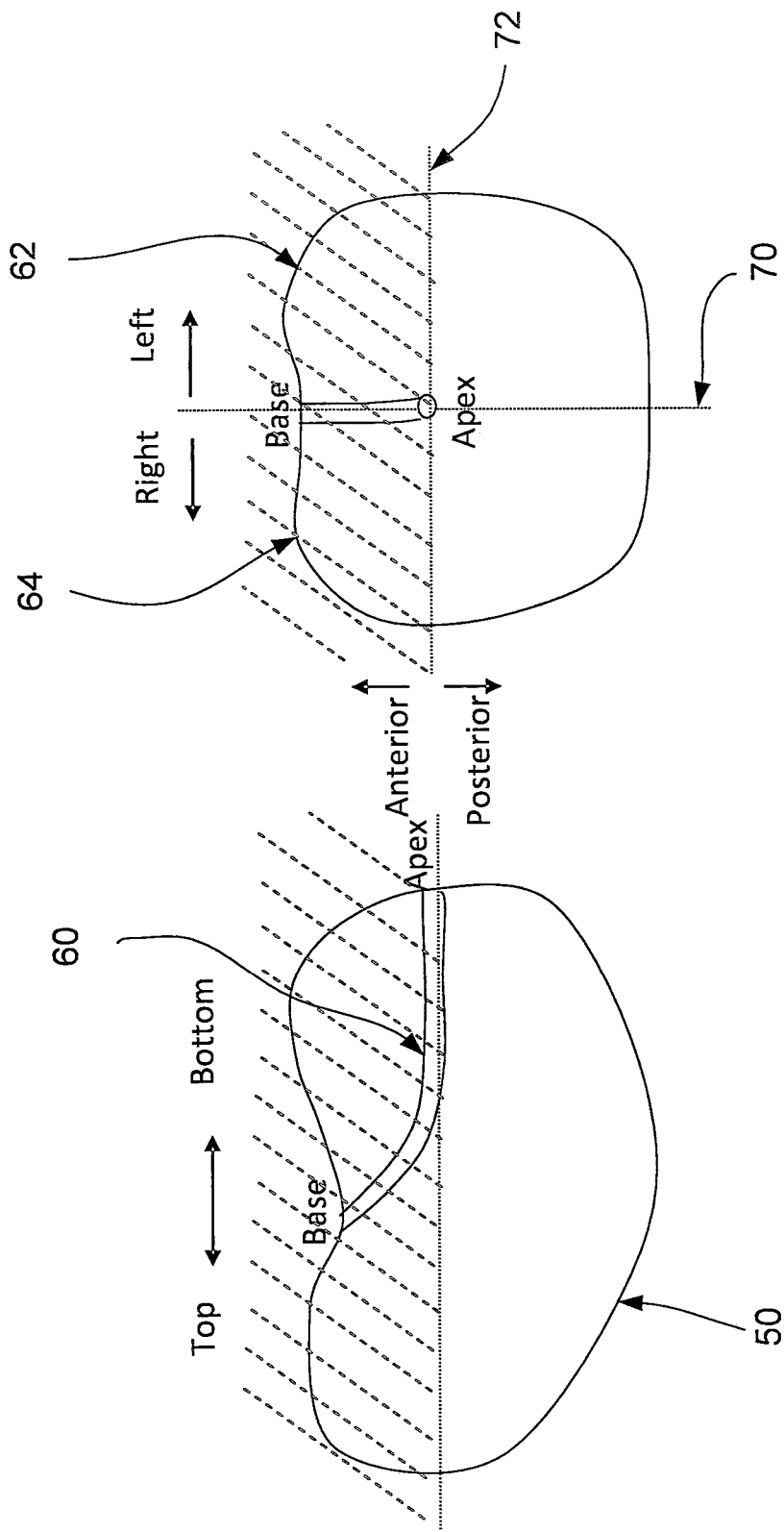
FIG. 4 represents urethra orientation in sagittal and transverse views of the prostate.

As show in FIG. 4, the urethra 60 passes through center of the prostate 50 and may be used as the main structure for identifying the zones of prostate. The urethra 60 lies in roughly mid-sagittal plane 70 and divides the prostate 50 into left and right regions 62, 64, respectively, when looked in a coronal (front to back) direction. Therefore, the first step is to determine the plane containing urethra center line. There are two ways in which it can be done:

1. At the beginning of the procedure, the user aligns the TRUS probe to the mid sagittal plane such that urethra 60 can be seen along the slice see top image FIG. 5. This image may be captured and a deformable model may be fitted on it to automatically detect the urethra 60, or it may be detected semi-automatically by user clicking on the base $P_0$ and apex points $P_2$.

2. The user finds urethra in reconstructed 3-D ultrasound image by browsing through 3-D scan using multi-planar view and finding the slice where the urethra can be seen. The user then clicks on a number of points along the urethra and the information is stored in 3-D world coordinate systems.

Once the information about central line of urethra 60 is available, it is easy to establish the mid-sagittal plane. The mid-sagittal plane can be defined by three non-collinear points $P_0$, $P_1$, $P_2$ along the urethra. The three points may be computed automatically for selection of most robust set of points. This may be done by selecting points $P_0$ and $P_2$ as the first and last points of the urethra center line and selecting point $P_1$ such that the triangle $P_0 P_1 P_2$ contains largest area. Let these points be $P_0$, $P_1$ and $P_2$ (see FIG. 4, which shows the sagittal (left) and transverse (right) views of the prostate 50 along with the urethra 60), where $P_0$ represents center of base, $P_1$ represents a point between base and apex, but not equal to either and $P_2$ represents Apex, respectively. Then the following vectors can be defined:

$$P_{10} = P_0 - P_1$$

$$P_{12} = P_2 - P_1$$

Figure 5:
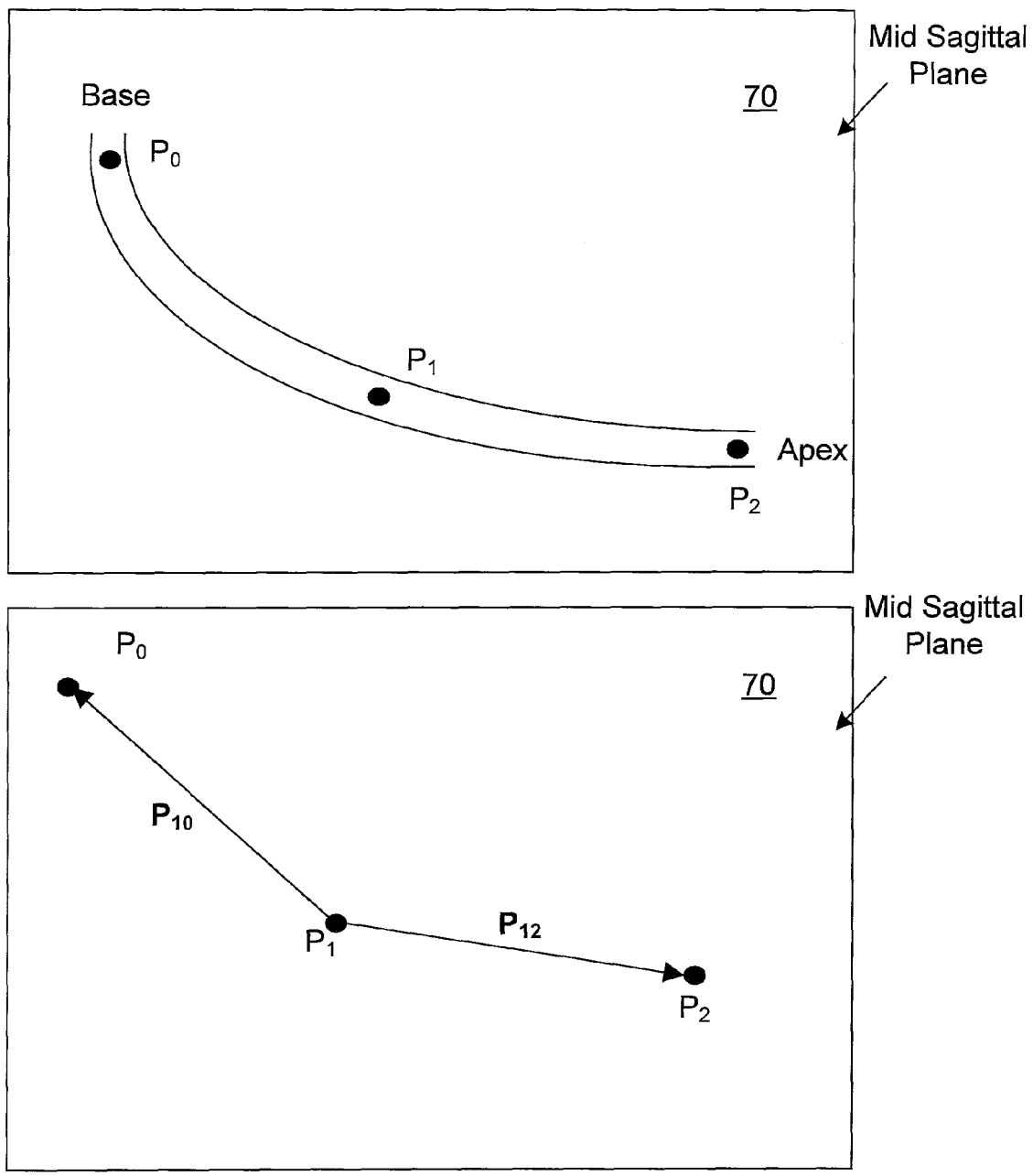
FIG. 5 shows automatic selection of points from urethra delineation for finding mid-sagittal plane.

See FIG. 5. Then, the normal to the plane in the right direction can be computed as:

$$n = (P_{12} \times P_{10}) / (\|P_{12}\| \|P_{10}\|)$$

Figure 6:
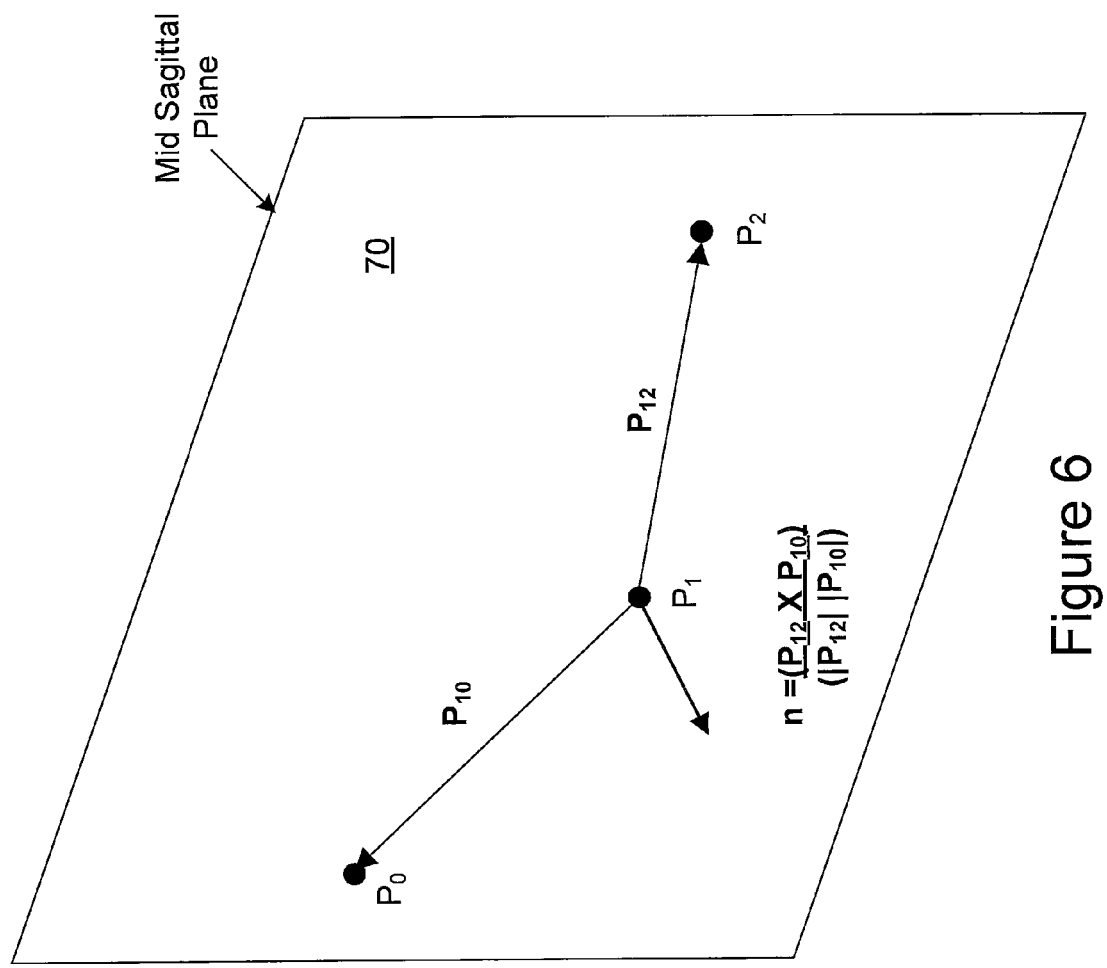
FIG. 6 shows the computation of normal to the mid-sagittal plane based on automatically selected points along urethra.

(see FIGS. 5 and 6). In the top of FIG. 5, three points P0, P1 and P2 defined along the urethra such that they are not collinear. In the bottom of FIG. 5, vectors P10 and P12 can be defined between the points. FIGS. 4 and 6 illustrates that normal to the mid-sagittal plane 72 can be found using cross product of the two vectors lying in the mid sagittal plane 70. The combination $(P_1, n)$ completely defines the mid-sagittal plane 70. Likewise, a combination $(P_1', n_1)$ and $(P_2', n_2)$ can be defined to represent planes that divide the line joining $P_0$ and $P_2$ such that:

$$n_1 = n_2 = (P_2 - P_0) / \|P_2 - P_0\|, \; P_1' = P_0 + (P_2 - P_0)/3 \text{ and}$$
$$P_2' = P_0 + 2*(P_2 - P_0)/3.$$

Then, plane $(P_1', n_1)$ (see line 76, FIG. 3) divides the prostate between base and mid regions of prostate and plane $(P_2', n_2)$ (see line 78, FIG. 5) divides the prostate between mid and apex region of the prostate along (e.g. mid-saggital plane 70) the line from base to apex.

The division between left and left-lateral may be done by dividing left part of the surface into half along a plane 78 in the direction of the normal to the mid-sagittal plane. Likewise, a division between right and right-lateral planes may be made, see plane 8, FIG. 3. Using same methodology, it is easy to distinguish between anterior and posterior regions of prostate along plane 72, if desired, using the plane $(P_1, (n \times n_1))$. See FIG. 4. The division of prostate 50 between different zones 54a-58d is beneficial in not only planning, but also in relating pathological findings to a region. With quality of life after prostate cancer treatment being a major concern, it is extremely important to know what region the cancer lies in so that focal therapy can be delivered only to the malignant part of the gland. The first step towards finding the cancer is to locate the cores taken during biopsy such that the pathology found can be localized to a region. In order to do that, it is of interest to label a sampled core as one of the zones identified before sending it for pathological studies. The presented invention does it automatically such that during planning, it computes which region the planned site lies in and the zone corresponding to the sampled core is also automatically computed. This is done by first computing the 3-D location of the sampled core (or planned site) and then doing the checks for the point being on one side or another for each plane mentioned. This way, a point can be independently categorized to lie in one of the zones. Example below illustrates how to compute whether a point lies on left side of prostate or right side. The same is extended to all the planes dividing prostate into regions.

Figure 7:
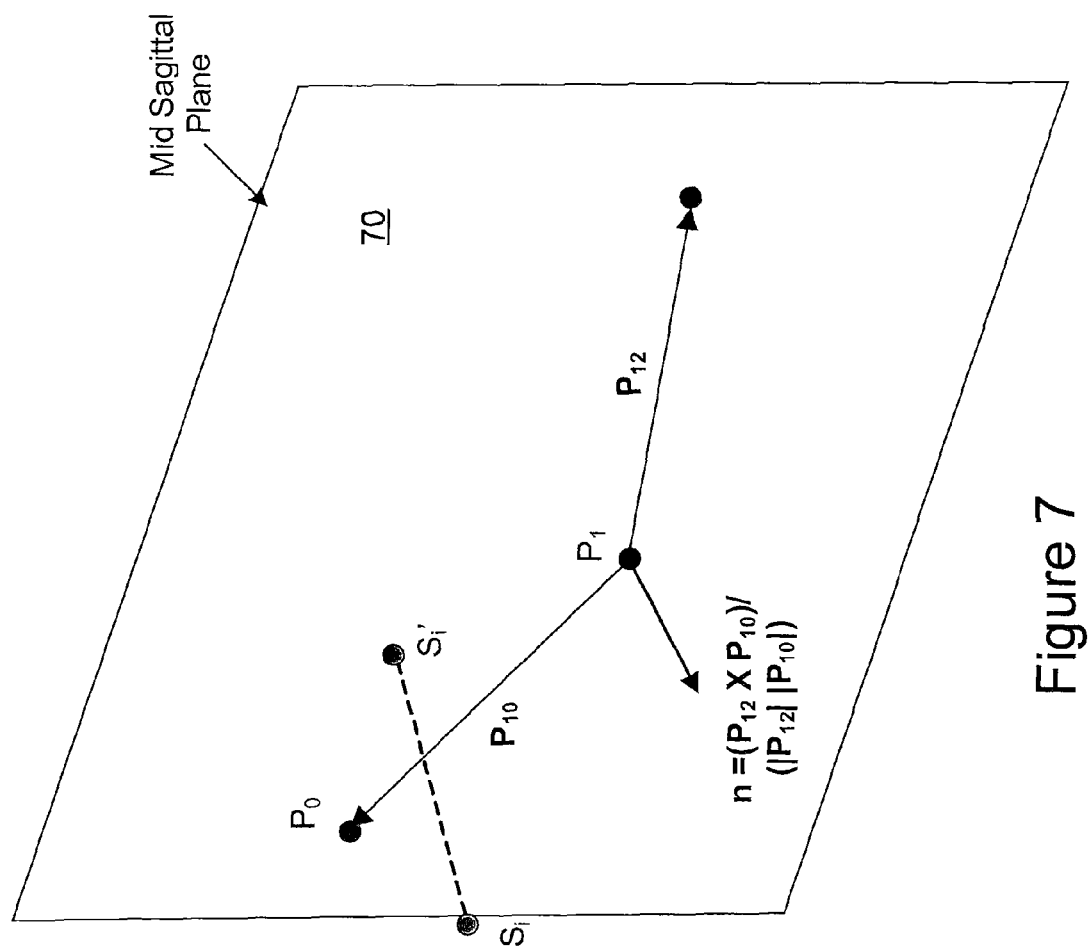

Given a planned site $S_i$, the following needs to be implemented to check whether the point lies on right side or left side of the plane:

Find closest point $S_i'$ on the plane from $S_i$ (see FIG. 7, which illustrates that given a biopsy site $S_i$, the projection of site to the plane $S_i'$ can be computed and the direction can be determined), using the following relation:

$$S_i' = S_i - S_i \cdot n / (n \cdot n) * n.$$

1. Compute vector $n_i' = (S_i - S_i) / \|S_i - S_i\|$. This represents the normal from the plane to the biopsy site.
2. Compute dot product $n_i \cdot n_i'$. If the value returned is 1, then the biopsy site is on right side of the urethra and if the value is −1, then the biopsy site $S_i$ is on left side of the urethra.

If the urethra is not available, an approximation may be made for dividing a prostate into various zones. For example, if the orientation of prostate image is known, the prostate may be divided into left and right about halfway in sagittal (left to right) direction and this may be treated as the mid-sagittal plane.

Distance Measurements During a Procedure

The invention contains subsystems to compute various distances during a procedure to aid in making clinical decisions. The following subsystems are discussed in more details:

1. Distance of planned point from prostate boundaries
2. Automatic plan based on uniform sampling of prostate
3. Distance measurement from prostate boundaries on live 2-D ultrasound image before needle insertion
4. Distance measurements from prostate boundaries after a needle insertion.

Distance of Planned Point from Prostate Boundaries

Figure 8:
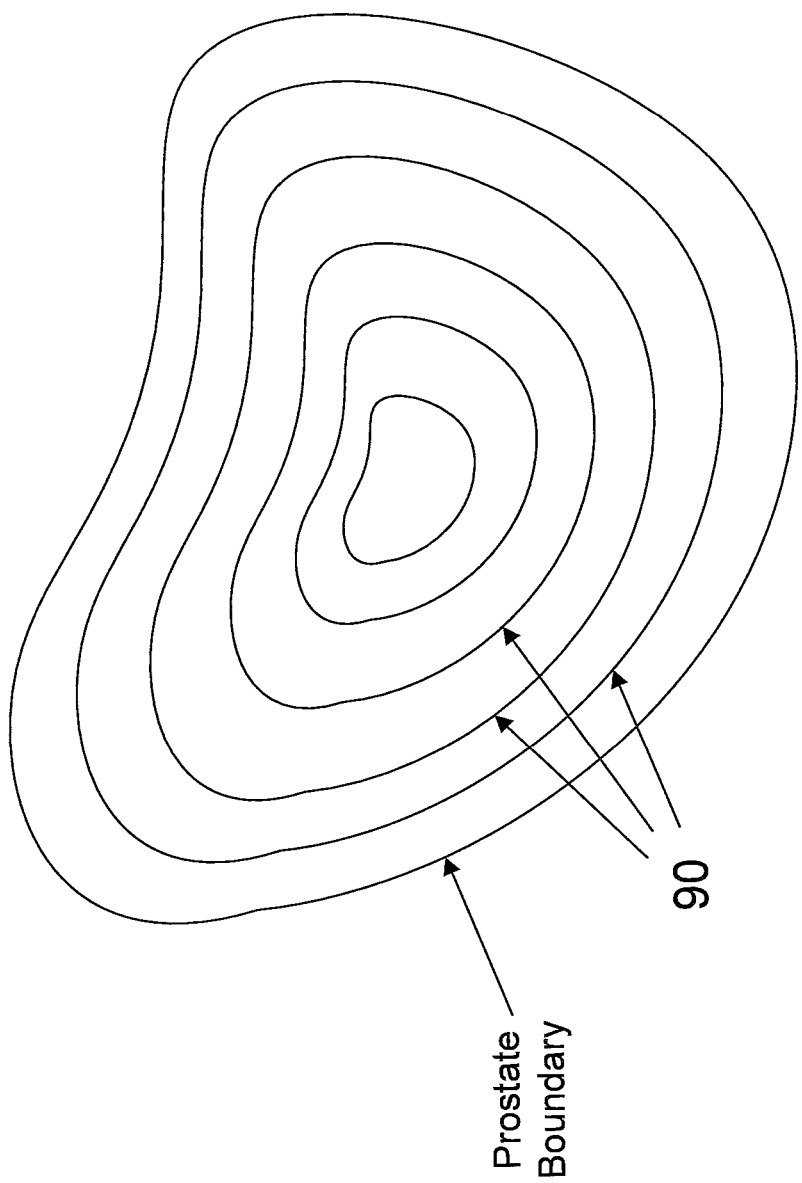
FIG. 8 represents an example of iso-surfaces that may be used for planning a biopsy based on the distance from prostate boundaries.

It is often desirable for some procedures to know the distances from the boundaries of prostate in 3-D such that a user can select a point accordingly for performing a procedure. For this purpose, the system uses computed prostate boundaries to compute iso-surfaces at user-selected distances and overlays them onto grayscale ultrasound (or any other modality image for planning) image such that for a selected point, the user knows the distances in true 3-D. Iso-surfaces represent the surfaces computed such that each surface is at a user-defined distance from the prostate boundaries. The displays of grayscale volumes typically include three orthogonal 2-D slices and it becomes hard for users to know the distances. The user may select more than one iso-surfaces to show at different distances from the boundaries. FIG. 8 shows one such example where iso-surfaces 90 computed at user-selected distances such that the user can use the distance information to plan a procedure.

Automatic Plan Based on Uniform Sampling of Prostate

Figure 9:
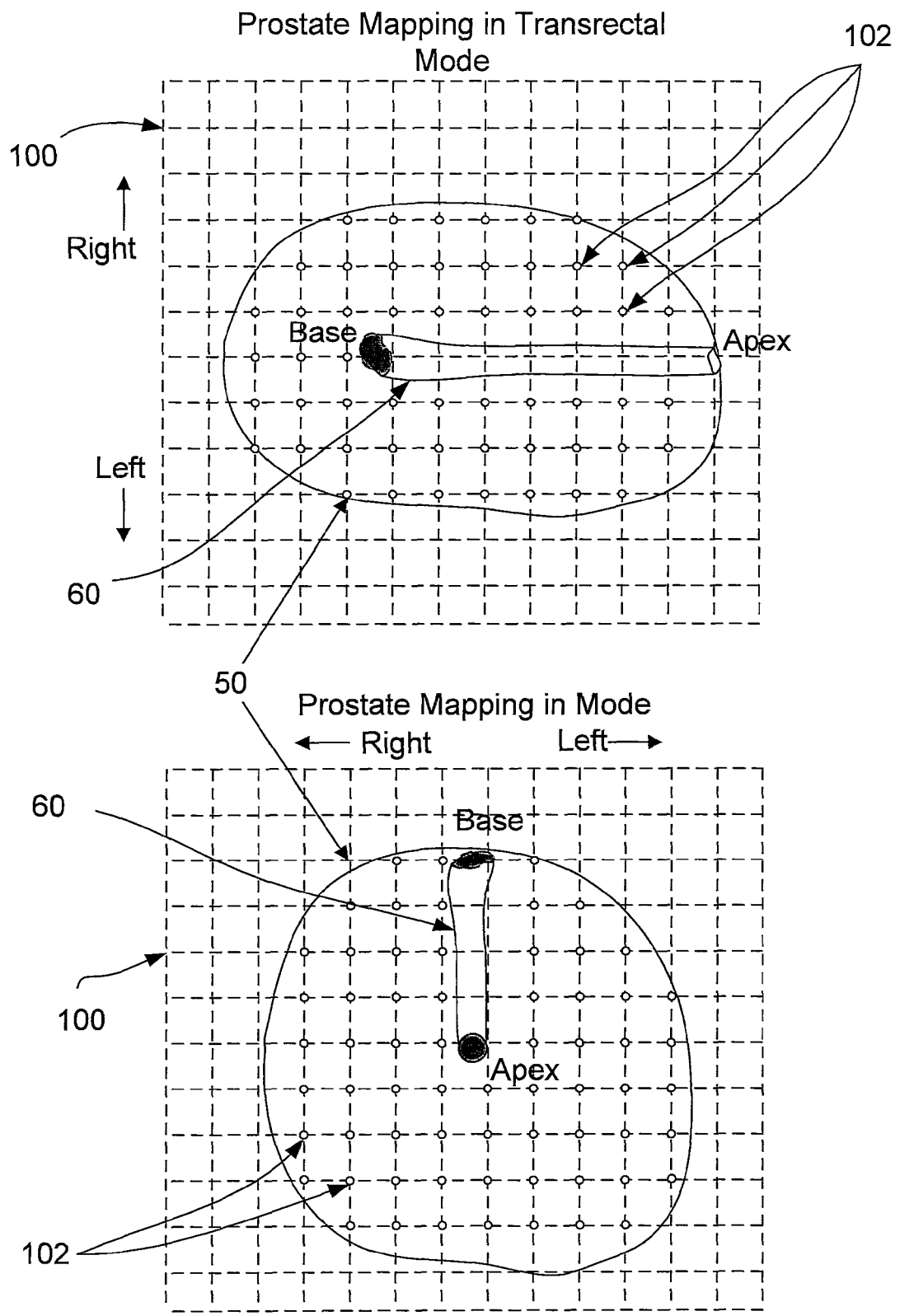
FIG. 9 shows a virtual grid overlaid on the prostate for aid in planning or biopsy.

The invention contains a subsystem that overlays a grid 100 with user-selected grid spacing over the prostate image 50 for a trans-rectal or trans-perineal procedure. The subsystem computes the grid 100 with lines spaced at the distance specified by the user and overlays it over the prostate grayscale image along the direction of view, as shown in FIG. 9. As shown, a virtual grid (or template) overlaid onto a) transrectal view of prostate and b) transperineal view of prostate. The grid may have a user-adjustable spacing and may automatically place planned sites on all grid elements lying inside the prostate that avoid certain regions. The user may then, either manually select sites based on this place for a plan, or automatically load a system generated plan customized to the prostate. The custom plan may be computed such that the user-specified regions such as urethra and neighboring organs and nerve bundles may be avoided during plan generation. This helps avoid accidental placement of needle for either biopsy or placing a bead at these sensitive locations during a procedure. FIG. 9 shows the plans for trans-rectal and trans-perineal procedures. The images above show the plan (small white circles 102 at intersection of grid lines) inside the prostate 50 that avoids the urethra. In such a procedure, the entire prostate is uniformly sampled at a user defined spacing to find and localize malignancies inside the prostate 50.

Distance Measurement from Prostate Boundaries on Live 2-D Ultrasound Image before Needle Insertion The invention contains a subsystem for providing visual feedback to the user for reaching a planned target for biopsy or dose delivery procedure. The system is calibrated to different needle types used for these procedures. For a given needle type, the system computes the throw distance and displays to the user how deep the needle should be inserted such that the selected target lies at center of the needle core. This ensures that the planned target site is sampled properly. The planned site is displayed only when the distance of the planned site from the current field of view of live ultrasound view is a preset small value (say, 5 mm). In addition to showing how deep the needle should be inserted before firing, the system also shows how deep the needle will be penetrated following firing. All the computations are done in 3-D frame of reference of the acquired image.

Figure 10:
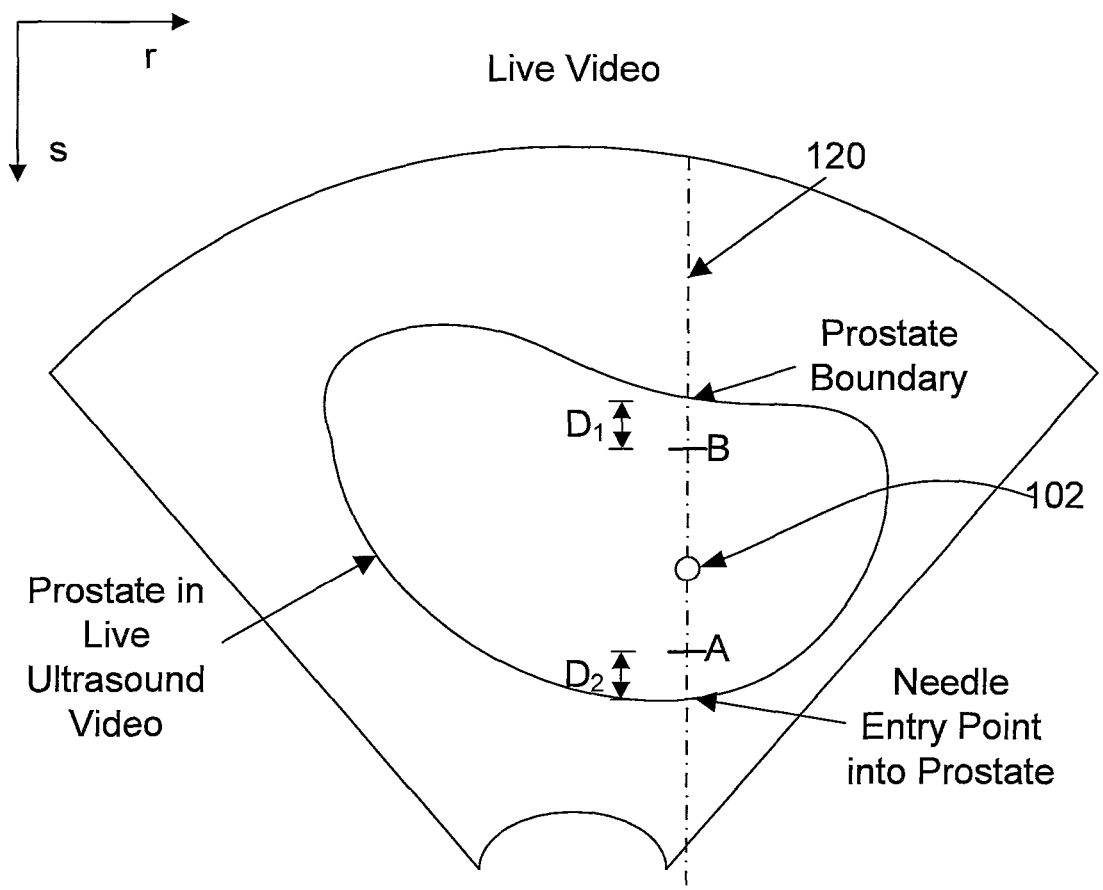
FIG. 10 shows various distance measurements obtained from prostate boundary estimation overlaid on a live ultrasound image.

For a biopsy procedure, the user shall reach the target point as such: first, using the 3-D image guidance, align the needle guide line or trajectory 120 with the target site. Then, as shown in FIG. 10, the target point 102 is displayed as a circle and two lines A, B appear on top and bottom of the live ultrasound video. The figure shows various distances in live image. Distance $D_2$ represents the distance of the point of firing from the top of the prostate as seen in the live view. Distance $D_2$ represents the distance from the top surface of prostate to the distal point of the core, Line A represents the depth of needle insertion before firing so that the center of the needle core contains the planned target site at its center. Line B represents the depth of needle penetration if it is fired after insertion up to point A. The bottom line A displays how deep the needle should be inserted while the top line B displays how deep the needle will go after firing. The user has to insert the needle up to the bottom line A and fire the needle gun to collect the sample.

Figure 11:
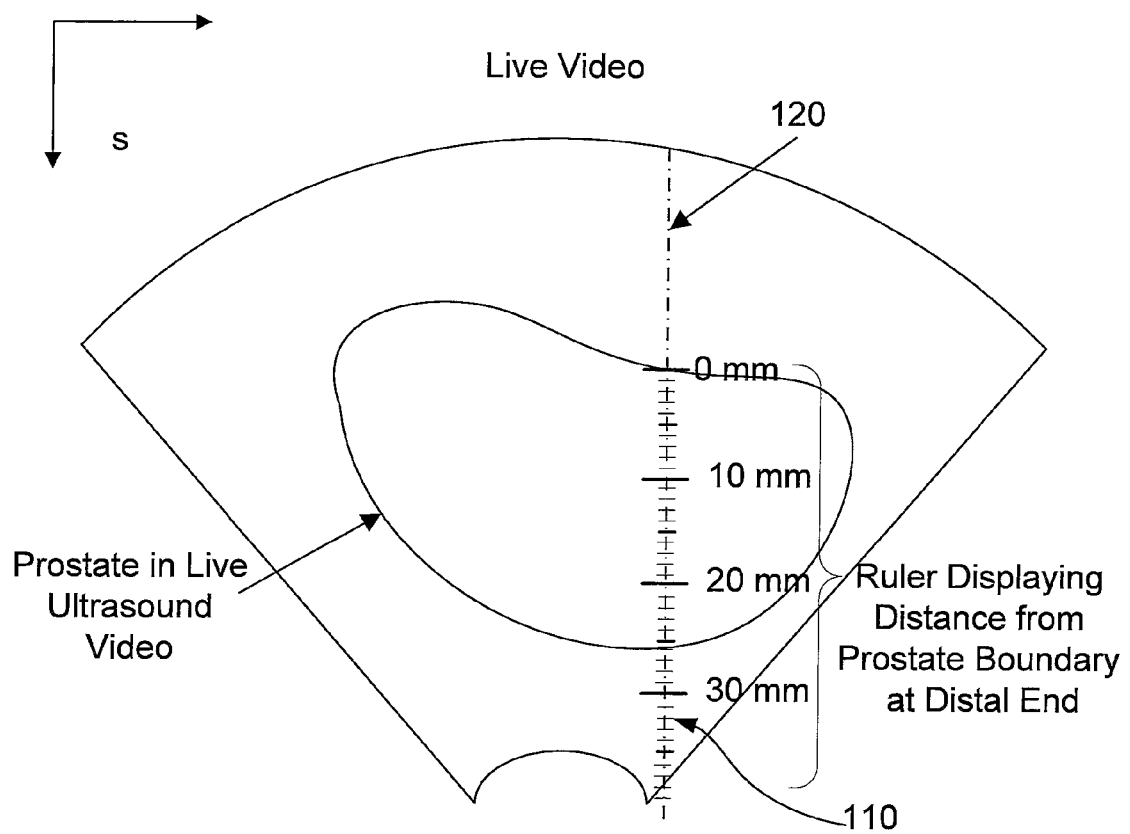
FIG. 11 represents a ruler overlaid on the live ultrasound image based on distance from distal end of prostate boundary along the needle trajectory.

It may not always be possible that the target site is selected such that the top line B does not go beyond prostate 50 and into the bladder or unwanted regions. In such cases, the system displays the top line B to be beyond prostate boundaries and user may not follow the protocol of inserting the needle up to the bottom line A. For these cases, a ruler 110 is displayed on the live view as shown in FIG. 11. The ruler shows the distance from the prostate boundary along the needle guide line 120. For a given needle guide line 120, as the user inserts the needle along the needle guide line 120, the system computes the needle trajectory in 3-D, finds intersection of the trajectory with the pre-computed prostate boundaries in 3-D and converts the intersection point back to frame of reference of the 2-D image. The distance can be shown in cm (or mm) from the point of intersection of the needle with the segmented surface. The system then drops down a ruler 120 from this point of intersection to give the user the distance measurement from the distal end of prostate such that the user can always see how far the needle tip is from the prostate boundaries and can thus avoid overshooting.

Distance Measurements from Prostate Boundaries after a Needle Insertion

In the presented invention, needle is segmented from the video captured during a sample extraction and the needle tip and trajectory are identified. Using tracking information, the 3-D location and trajectory of the needle can be identified in frame of reference of the 3-D image by applying transformation to the needle tip and entry points. The prostate surface is internally represented as a set of triangles connected together to form a closed surface. The intersection point of surface along the line of needle trajectory is computed by the system. The Euclidean distance can be directly computed from the needle tip to the intersection point on the surface.

Figure 12:
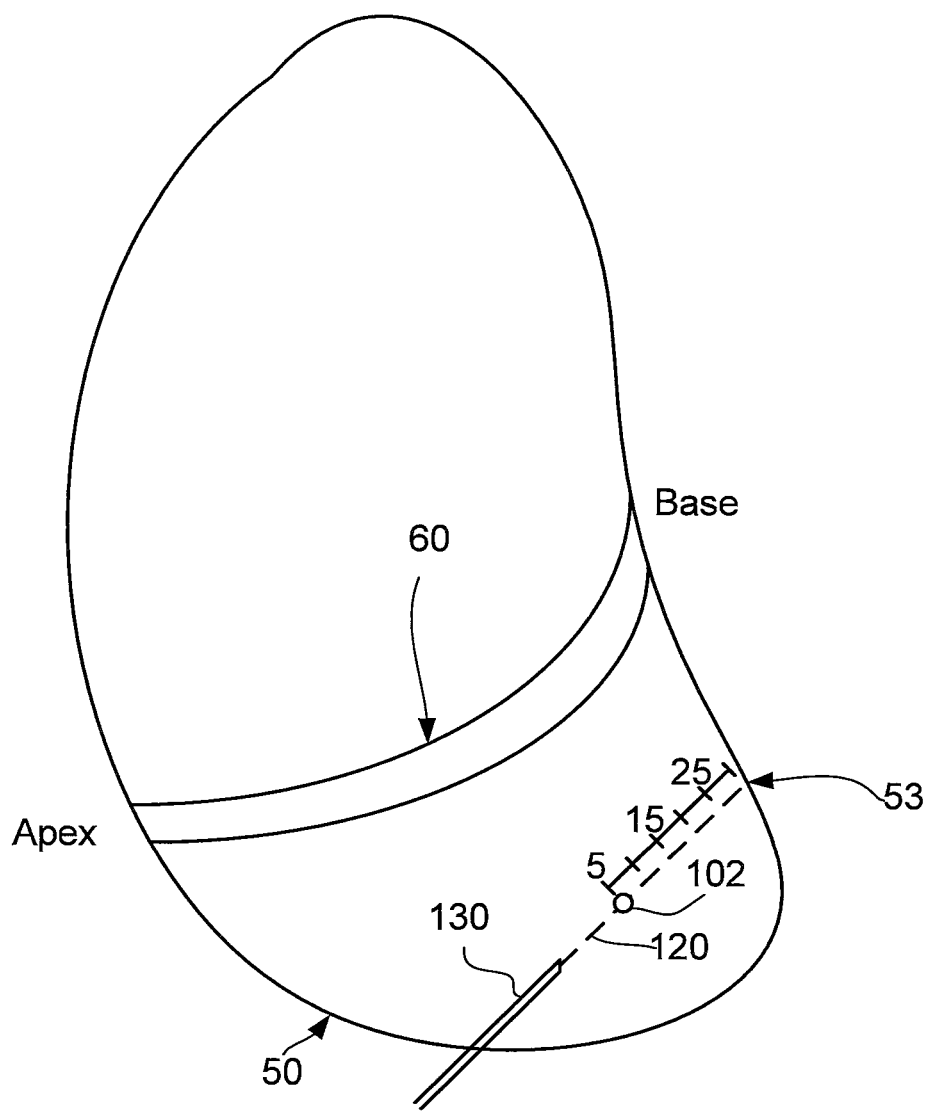
FIG. 12 shows the measurements overlaid on 3-D prostate model after a biopsy.

The line 120 from the tip of needle 130 to the surface 53 is displayed as a dotted yellow line for visual verification. The distance is displayed in mm along the line as shown in FIG. 12, which shows the display of needle tip distance from the surface of prostate along the needle trajectory. The figure shows the display for the sampled biopsy site (102), the distance was computed to be 11.0 mm and the dotted line represents the trajectory up to the point of intersection. The following process is used for computing distance from top:
1. Compute needle trajectory by transforming two points on needle guide into 3-D frame of reference.
2. For each triangle in prostate surface:
    a. Find intersection of line with the triangle plane
    b. Find whether intersection point lies inside the triangle or outside
    c. If intersection lies outside, move to next triangle
    d. If intersection found, find whether intersection is along the needle trajectory in positive direction. This can be tested by computing dot product of triangle normal with the needle trajectory. The sign of dot product determines whether triangle is facing in to or facing away from the needle.
    e. If intersection lies inside and towards distal end of the needle, compute perpendicular distance.

Alternatively, if the intersection of the surface is already computed with the current plane, then the calculation can be performed in 2-D frame of reference of live image. FIG. 12 shows the distances with reference to the prostate surface 50.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

The invention claimed is:

1. A method for use in transrectal ultrasound guided biopsy, comprising:
    receiving a 3D image of a prostate gland at a processor;
    processing said 3D image to delineate a urethra in the 3D image of said prostate gland, wherein the urethra is delineated using a series of at least three non-collinear control points identified in at least a first image of the prostate gland, at least a first of said at least three non-collinear control points represents a first intersection of the urethra with a surface of the prostate gland and at least a second of said at least three non-collinear control points represents a second intersection of the urethra with the surface of the prostate gland;

using the delineated urethra, processing the 3-D image to define a mid-plane dividing the prostate gland into first and second lateral portions;

based on said defined mid-plane, generating at least one plane transverse to the mid-plane such that the prostate gland is divided into at least one upper portion and at least one lower portion, wherein said mid-plane and said at least one plane define a plurality of zones in said 3-D image of said prostate gland;

generating a prostate zone image such that said plurality of zones are displayed on the 3-D image of the prostate gland; and generating at least one biopsy target point in at least one of said plurality of zones, wherein said biopsy target point is displayed on said prostate zone image.

2. The method of claim 1, wherein each said biopsy target point comprises a centroid of an area corresponding to one of said plurality of zones.

3. The method of claim 1, further comprising:
generating at least first and second planes transverse to the mid-plane dividing said prostate gland image into upper, mid and lower portions.

4. The method of claim 1, further comprising:
generating first and second parallel planes disposed substantially parallel to said mid-plane, wherein said parallel planes divide said prostate gland into at least four lateral zones.

5. The method of claim 1, wherein said at least three non-collinear control points define said mid-plane.

6. The method of claim 1, wherein delineating comprises:
identifying a first point that represents said first intersection of the urethra with the surface of said prostate gland;
identifying a second point that represents said second intersection of the urethra with the surface of said prostate gland; and
identifying a third point that represents a point within said urethra between said first point and said second point.

7. The method of claim 1, further comprising:
overlaying at least one biopsy target point of said prostate zone image on a 2-D image acquired from an ultrasound transducer; and
generating an output image of said at least one biopsy target displayed on said 2-D image.

8. The method of claim 7, wherein overlaying comprises applying a transformation from a 3-D frame of reference of said prostate zone image to a frame of reference of the 2-D ultrasound image.

9. The method of claim 7, further comprising:
displaying a needle trajectory line on said output image, where said needle trajectory line corresponds to a needle insertion trajectory of a biopsy needle supported by a needle guide.

10. The method of claim 9, further comprising:
generating a first line on said needle trajectory line of said output image a first distance from a surface boundary of said prostate representing a depth of needle insertion before firing; and
generating a second line on said needle trajectory line of said output image a second distance from the surface boundary of said prostate representing a depth of needle insertion after firing.

11. The method of claim 10, wherein said biopsy target point is disposed between said first line and said second line.

* * * * *